United States Patent [19]

Harris

[11] 4,290,302

[45] Sep. 22, 1981

[54] BIAXIAL SHEAR FORCE GAUGE

[75] Inventor: Clarence J. Harris, Lansdowne, Pa.

[73] Assignee: The United States of America as represented by the Secretary of the Air Force, Washington, D.C.

[21] Appl. No.: 129,858

[22] Filed: Mar. 13, 1980

[51] Int. Cl.³ .......................................... G01N 17/00
[52] U.S. Cl. ......................................... 73/86; 73/841
[58] Field of Search ............... 73/841, 15.6, 86, 133 R

[56] References Cited

U.S. PATENT DOCUMENTS 3,460,383 8/1969 Padera .................................. 73/147
4,059,011 11/1977 Reiss .............................. 73/133 MC

OTHER PUBLICATIONS

Cherela, O. B. et al., Device for Testing ... High Temperatures, May 1975, p. 1704, Industrial Laboratory, vol. 40, No. 11.

Primary Examiner—Jerry W. Myracle

Attorney, Agent, or Firm—Donald J. Singer; Arsen Tashjian

[57] ABSTRACT

A gauge for use with a test specimen that is made of a preselected ablative material to be tested, and that is in a high temperature gaseous flow (i.e., a hot environment) which is capable of ablating the test specimen, and which also is capable of inducing, and of exerting on the test specimen, a resultant shear force (i.e., a shear force vector) that comprises constituent axial and lateral forces. The test specimen is bonded on the mounting surface of a block member (of the gauge) that is positioned on bearings, within a housing, for movement in axial and lateral directions. A plurality of force sensors are positioned around the perimeter of the block member, and the constituent axial and lateral forces of the resultant shear force that is acting on the test specimen are transmitted to these sensors. The components of the gauge are protected from shock by their structure and positional relationship, and are protected from overheating by the water-cooling of the housing. Unlike the prior art, the gauge also can be used in a cold, rather than a hot, environment.

10 Claims, 4 Drawing Figures

BIAXIAL SHEAR FORCE GAUGE

STATEMENT OF GOVERNMENT INTEREST

The invention described herein may be manufactured and used by or for the Government for governmental purposes without the payment of any royalty thereon.

BACKGROUND OF THE INVENTION

This invention relates to a biaxial shear force gauge and, more particularly, to such a guage which is adapted for use in measuring the shear force vector (magnitude and direction) on materials undergoing ablation in a high temperature gaseous flow.

In the prior art, shear force gauges as such are well known. However, it is fair and accurate to say, that the known prior art shear force gauges are for use in a cold environment, in contradistinction to a hot environment. In fact, in the prior art there is not any shear force gauge that is useable, or that can be adapted to be used, in the necessarily hot environment of a material undergoing ablation. Therefore, what is needed in the art, and is not presently available, is a shear force gauge which can be used in an ablation-causing hot environment.

I have invented such a needed shear force gauge; and, by fulfilling that need, I have significantly advanced the state-of-the-art.

SUMMARY OF THE INVENTION

My invention specifically pertains to a biaxial shear force gauge for use with a specimen of preselective ablative material which is in a high temperature gaseous flow (i.e., a hot environment) that is capable of exerting a resultant shear force (i.e., a shear force vector), which in turn comprises constituent axial and lateral forces, on the top surface of the specimen, and with the high temperature gaseous flow also being capable of ablating the specimen.

Accordingly, the principal object of my invention is to teach the structure of a preferred embodiment of the above-described biaxial shear force gauge, thereby permitting the axial and lateral constituent forces of the resultant shear force to be measured in the above-described hot environment.

This object of my invention, as well as related objects of my invention (such as adaptability of my invention for use in a cold environment), will become readily apparent after a consideration of the description of my invention, together with reference to the Figures of the drawing.

DESCRIPTION OF THE PREFERRED EMBODIMENT

Figure 1:
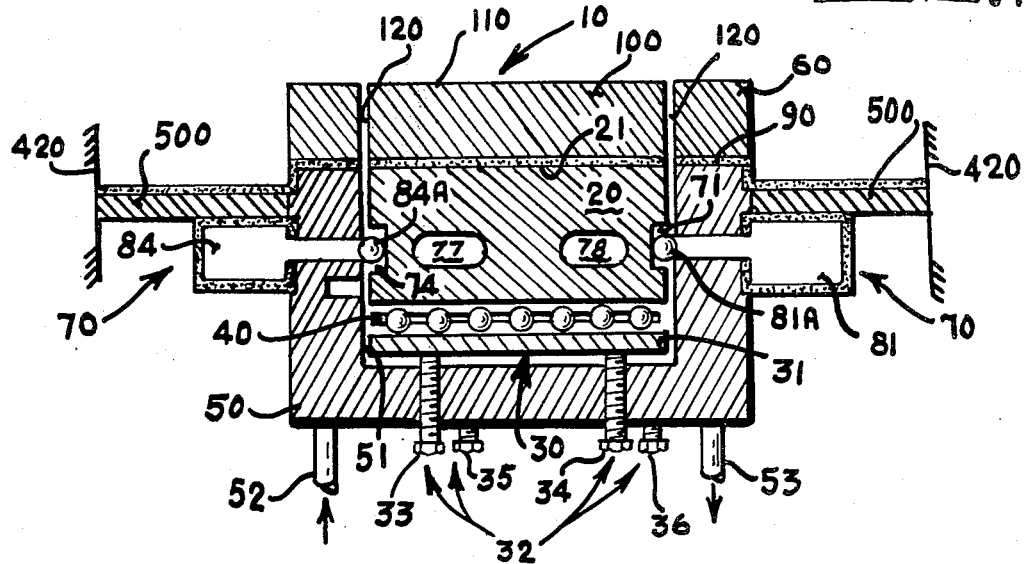
FIG. 1 is a side elevation view, in simplified pictorial and schematic form, of a preferred embodiment of the invention in its working high temperature environment.
Figure 2:
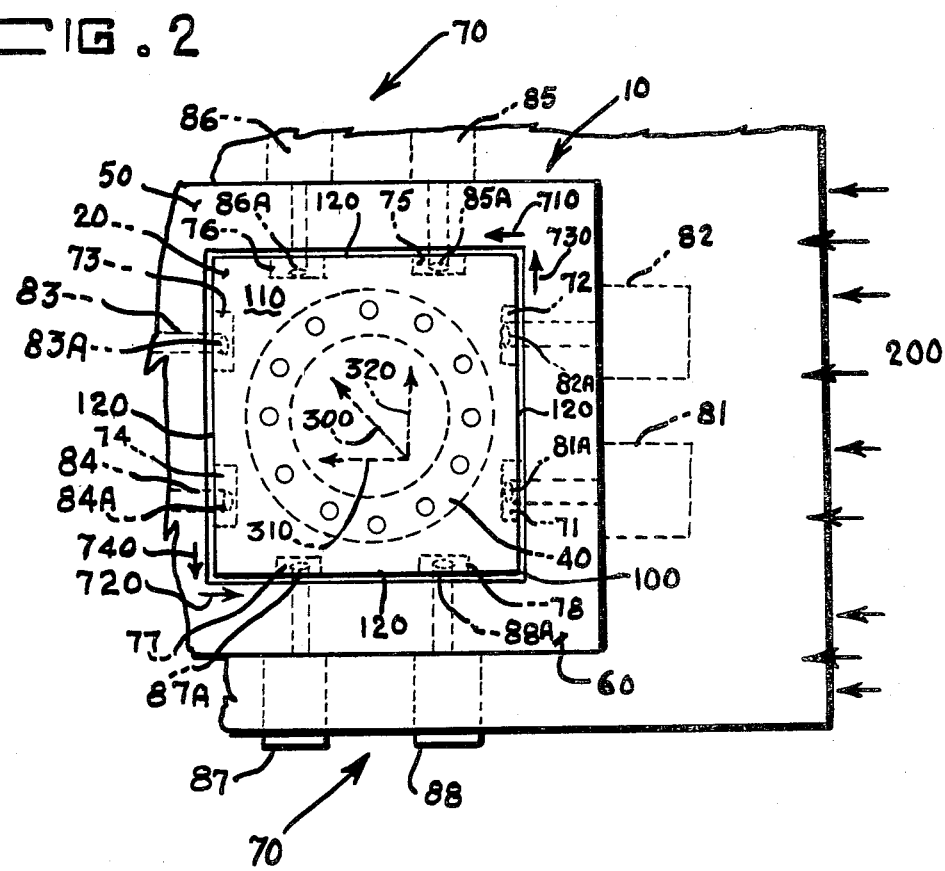
FIG. 2 is a top plan view, partially fragmented and in simplified pictorial and schematic form, of the preferred embodiment shown in FIG. 1, also in its working environment.

With reference to FIGS. 1-3, inclusive, therein is shown, in various views, the preferred embodiment 10 of my invention: a biaxial shear force gauge.

Figure 3A:
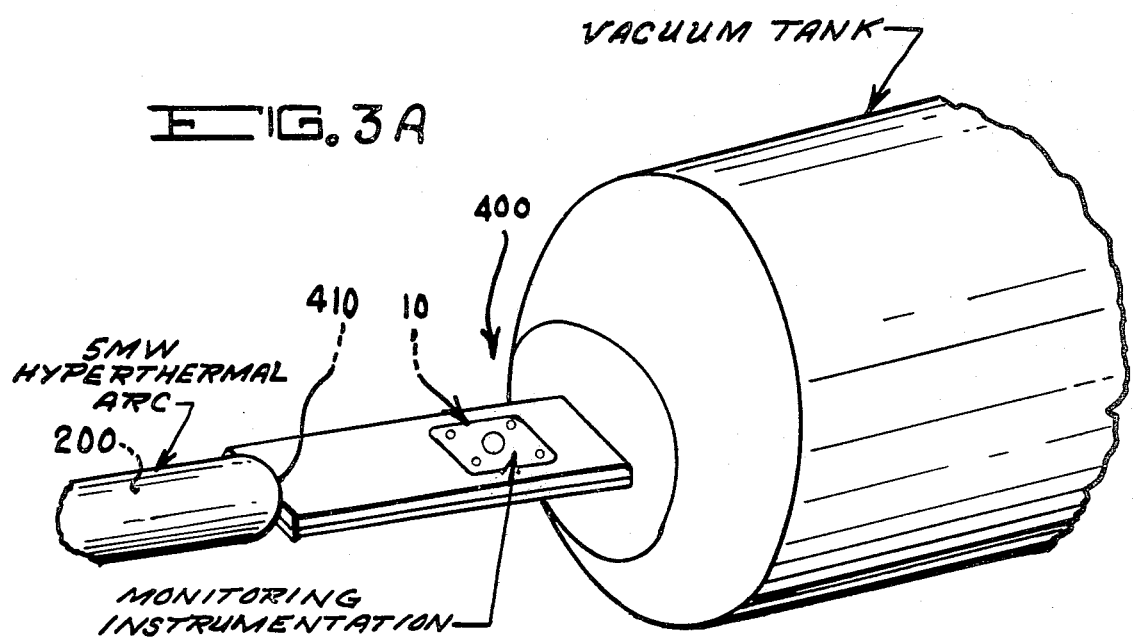
FIGS. 3A and 3B show the preferred embodiment, in schematic form, in a typical application, i.e., in use in a facility in which there exists a high temperature gaseous flow, as described hereinbefore.
Figure 3B:
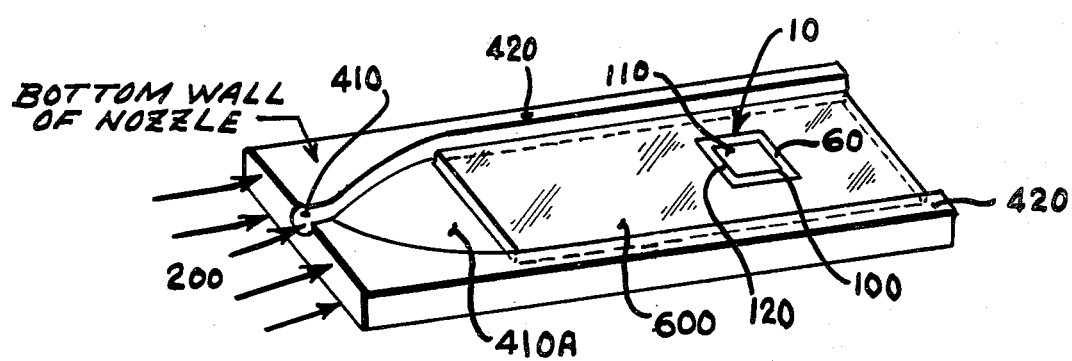

As a preliminary matter, it is to be noted and remembered that my inventive biaxial shear force gauge 10 (best shown in FIGS. 1 and 2), as described and shown herein, is adapted for use with a test specimen (such as 100, FIGS. 1, 2 and 3B) of a preselective ablative material which has a top surface (such as 110, FIGS. 1, 2 and 3B) and a perimeter surface 120, FIGS. 1, 2 and 3B), where this test specimen 100 is in a high temperature gaseous flow (such as 200, FIGS. 2 and 3B) which is capable of exerting a resultant shear force or, more precisely, a shear force vector (such as 300, FIG. 2) that, in turn, comprises a constituent axial force (such as 310 FIG. 2) and a constituent lateral force (such as 320, FIG. 2) on the top surface 110 of the specimen 100, and where the high temperature gaseous flow 200 is also capable of ablating, but need not ablate, the test specimen 100.

In the most basic and generic structural form, my inventive biaxial shear force gauge 10 comprises: a low inertial mounting block member 20, FIGS. 1 and 2, that has a top surface 21 upon which the test specimen 100 of ablative material is mounted, with this member 20 being free to move in axial and lateral directions (such as, respectively, axial directions 710 and 720 and lateral directions 730 and; 740, best shown in FIG. 2); a bottom support assembly 30, FIG. 1, that is disposed below, and is in alignment with, the mounting block member 20, with the assembly 30 including a bottom support member 31, FIG. 1, and means (generally designated 32 in FIG. 1) for leveling the bottom support member 31; a linear thrust ball bearing member 40, FIG. 1, that is interposed between, and that is in abutting contact with, the bottom surface of the mounting block member 20 and the top surface of the bottom support member 31 of the bottom support assembly 30; a water-cooled container/housing 50, FIGS. 1 and 2, that has an opening (such as 51, FIG. 1) in which the mounting block member 20, the linear thrust ball bearing member 40, and the bottom support assembly 30 are disposed and housed, as shown in FIG. 1; a housing guard member 60, FIGS. 1, 2 and 3B, which is made of the same ablative material that the first specimen 100 is made of, with this housing guard member 60 shaped and sized to surround, and disposed so as to surround, the perimeter surface 120 of the test specimen 100 (such as is best shown in FIGS. 1, 2 and 3B), and with this housing guard member 60 also simultaneously mounted on the top surface of the water-cooled container/housing 50 (as is best shown in FIG. 1), with a gap, FIG. 1, between this housing guard member 60 and the perimeter surface 120 of the test specimen 100; and, a means (generally designated 70) for detecting and measuring any axial and lateral constituent forces (such as 310 and/or 320, FIG. 2) of the resultant shearing force (or vector) 300, FIG. 2, that are exerted on the top surface 110 of the test specimen 100 of the preselected ablative material by the high temperature gaseous flow 200, FIGS. 2 and 3B.

More specifically, and as a matter of preference and not of limitation, the low inertial mounting block member 20 is made of polished, hardened, and reduced-mass aluminum; the bottom support member 31 of the bottom support assembly 30 is made of polished stainless steel;

the means 32 for leveling the bottom support member 31 includes a plurality of jack leveling screws, such as representative ones 33-36, inclusive, FIG. 1; and the water-cooled container/housing 50 is made of copper and has an inlet 52 and an outlet 53.

Also more specifically, and with particular reference to means 70, FIGS. 1 and 2, for detecting and measuring any axial and lateral constituent forces (such as 310 and 320, FIG. 2) of the resultant shearing force 300 (i.e., the shearing force vector), FIG. 2, that are exerted on the top surface 110 of the test specimen 100 of the preselected ablative material by the high temperature gaseous flow 200, FIG. 1, this means 70 preferably comprises: a plurality of axial and lateral highly polished slots (such as, respectively, representative axial slots 71-74, FIG. 2, and representative lateral slots 75 and 76, FIG. 2, and 77 and 78, FIGS. 1 and 2 in the mounting block number 20; and a plurality of axial and lateral force sensors (such as, respectively, representative axial force sensors 81 and 84, FIGS. 1 and 2, and 82 and 83, FIG. 2, and representative lateral force sensors 85-88, FIG. 2), with one force sensor for each highly polished slot in the mounting block member (i.e., an axial force sensor for each axial slot, and a lateral force sensor for each lateral slot), and with each force sensor including a low friction ball bearing (i.e., ball bearings 81A-88A, FIG. 2, for force sensors 81-88, respectively) that is in contact with that sensor's respective highly polished slot and also is simultaneously connected to that sensor (e.g., as shown in FIGS. 1 and 2, low friction ball beaing 81A of force sensor 81 is in contact with highly polished slot 71 and, of course, is connected by suitable conventional means, i.e., a connecting member, to force sensor 81).

As can be readily surmised from the foregoing, and as a matter of preference and not of limitation, the plurality of jack leveling screws comprises four of these leveling screws, i.e., 33-36, inclusive, FIG. 1; the plurality of axial, and of lateral, highly polished slots in the mounting block member 20, FIGS. 1 and 2, comprises eight such slots, i.e., 71-78, inclusive, FIG. 2; and the plurality of axial, and of lateral, force sensors comprises eight such force sensors, i.e., 81-88, inclusive, FIG. 2, with one such sensor for each of the slots.

Also as a matter of preference, the test specimen 100 of the preselected ablative material is mounted on the low inertial mounting block member 20 with the use of a bonding material (such as is designated 90, FIG. 1), and the housing guard member 60 of the same preselected ablative material is mounted on the water-cooled container/housing 50 also with the use of a bonding material (also such as designated 90, FIG. 1). The bonding (and mounting) of test specimen 100 and of the housing guard member 60 is structurally accomplished by the use of any conventional useable bonding material, preferably a room temperature vulcanizing bonding material.

Now, with specific reference to FIGS. 3A and 3B, there is shown the preferred embodiment 10 of my invention, in simplified schematic form and in a typical application, i.e. in use in a facility 400, FIG. 3A, in which there exists a high temperature gaseous flow 200 (i.e., a hot environment) that is capable of exerting a resultant shear force 300 (i.e., a shear force vector), FIG. 1, which in turn comprises constituent axial and lateral forces, such as 310 and 320, FIG. 2, on the top surface 110, FIGS. 1 and 2, of the test specimen 100, FIGS. 1 and 2, and with the high temperature, gaseous flow 200 also being capable of ablating the test specimen 100.

Still with reference to FIGS. 3A and 3B, the 5 mw hyperthermal arc apparatus, and the oppositely disposed vacuum tank, in combination generate the high temperature gaseous flow 200 described hereinbefore, which then flows through the two-dimensional nozzle 410 that is within, and that is interposed between, the arc apparatus and the vacuum tank of the facility 400. It is to be noted that, to reduce any vibration effects from the facility 400, FIG. 3A, the already-described gauge 10, FIGS. 1 and 2, is shock-mounted by suitable means 500, FIG. 1, to the nozzle wall 420, FIGS. 3B and 1, and simultaneously also to the water-cooled container/housing 50, as shown in FIG. 1.

It is to be noted that the floor 410A, FIG. 3B, of the nozzle 410, FIG. 3B, may be made also of the same preselected ablation material 600 (as the test specimen 100 and the housing guard member 60, FIGS. 1, 2 and 3B, are made of) to minimize the possibility of differential ablation taking place at the leading edge of the test specimen 100, FIGS. 1, 2 and 3B.

It is also to be noted: that the low friction ball bearing (such as representative one 81A, FIGS. 1 and 2) of each force sensor (such as representative one 81, FIGS. 1 and 2) maximizes the ability of each force sensor to measure only a compressive load and, thereby, minimizes cross-coupling between the axial and lateral measurements; that both transient type and steady-state type of sensors (or of transducers) may be used simultaneously in the gauge 10, FIGS. 1, 2 and 3B during any test, such as is shown in FIGS. 3A and 3B; and that the sensing elements of the gauge 10 are adequately protected from heating by the ablation material 100 and 60, FIGS. 1, 2 and 3B, and by water-cooling with the container/housing 50, FIG. 1, and, if used, also by the ablation material 600, FIG. 3B.

MANNER OF OPERATION OF THE PREFERRED EMBODIMENT

The manner of operation and of use of the preferred embodiment 10, FIGS. 1, 2 and 3B, of the invention can be easily ascertained by any person of ordinary skill in the art from the foregoing description, coupled with reference to the contents of the Figures of the drawings. Accordingly, no step-by-step, cause-and-effect description of the action of the interdependent and cooperating components of the invention is deemed necessary. However, it is respectfully pointed out to those of ordinary skill in the art that the invention permits the accurate measurement of the axial and lateral forces 310 and 320, FIG. 2, resulting from the shear vector 300, FIG. 2, acting on the top surface 110 of the test specimen 100 that is made of the preselected ablative material, irrespective of whether or not ablation actually takes place; and, that these measurements, in turn, can be used to define the roll torgue characteristics of the ablating material.

CONCLUSION

It is abundantly clear from all of the foregoing, and from the contents of the Figures of the drawings, that the desired principal object of the invention, as well as other related objects of the invention, have been achieved.

It is to be noted that, although there have been described and shown the fundamental and unique features of the invention as applied to a preferred embodiment, adapted for a particular use, various other embodiments, variations, adaptations, substitutions, additions, omissions, and the like may occur to, and can be made by, those of ordinary skill in the art, without departing from the spirit of the invention. For example: (a) the bottom support member 31 of the bottom support assembly 30 can be made of polished tungsten, rather than of polished stainless steel; (b) the inventive gauge 10 can be used in a cold environment, rather than the hot environment described herein; and (c) the inventive gauge 10 permits the accurate measurement of the axial and lateral forces resulting from the shear vector acting on the surface of the test specimen of a preselective ablative material, with or without ablation actually occurring.

What is claimed is:

1. A biaxial shear force gauge for use with a test specimen made of a preselected ablative material and having a top surface and a preimeter surface, wherein said test specimen is in a high temperature gaseous flow which is capable of ablating said test specimen, and which also is capable of inducing, and of exerting on said top surface of said test specimen, a resultant shear force that comprises constituent axial and lateral forces, comprising:
   a. a low inertial mounting block member having a top surface upon which said test specimen of preselected ablative material is mounted, wherein said mounting block member is free to move in axial directions and in lateral directions;
   b. a bottom support assembly disposed below, and in alignment with, said mounting block member, wherein said bottom support assembly includes a bottom support member and a means for leveling said bottom support member;
   c. a linear thrust ball bearing member interposed between, and in abutting contact with, said mounting block member and said bottom support member of said bottom support assembly.
   d. a water-cooled container/housing having an opening in which said mounting block member, said linear thrust ball bearing member, and said support assembly are disposed and housed;
   e. a housing guard member made of said same preselected ablative material as said test specimen, and shaped and sized to surround, and disposed so as to surround, said perimeter surface of said test specimen of said preselected ablative material, wherein this housing guard member is simultaneously mounted on said water-cooled container/housing;
   f. and, means for detecting and measuring any axial and lateral constituent forces of said resultant shearing force that are exerted on said top surface of said test specimen of said preselected ablative material by said high temperature gaseous flow.

2. A biaxial shear force gauge, as set forth in claim 1, wherein said low inertial mounting block member is made of polished, hardened, reduced-mass aluminum.

3. A biaxial shear force gauge, as set forth in claim 2, wherein said said bottom support member of said bottom support assembly is made of polished stainless steel.

4. A biaxial shear force gauge, as set forth in claim 3, wherein said means for leveling said bottom support member includes a plurality of jack leveling screws.

5. A biaxial shear force gauge, as set forth in claim 4, wherein said water-cooled container/housing is made of copper.

6. A biaxial shear force gauge, as set forth in claim 5, wherein said means for detecting and measuring any said axial and lateral constituent forces of said resultant shearing force that are exerted on said top surface of said test specimen of said preselected ablative material by said high temperature gaseous flow includes:
   a. a plurality of axial, and lateral, highly polished slots in said mounting block member;
   b. and, a plurality of axial and lateral force sensors, with one said sensor for each one of said highly polished slots in said mounting block member, and with each said sensor including a low friction ball bearing in contact with said sensor's respective highly polished slot and also simultaneously connected to said sensor.

7. A biaxial shear force gauge, as set forth in claim 6, wherein:
   a. said plurality of jack leveling screws comprises four of said screws;
   b. said plurality of axial, and lateral, highly polished slots in said mounting block member comprises eight such slots;
   c. and, said plurality of axial and lateral force sensors comprises eight such sensors, with one such sensor for each of said eight axial, and lateral, highly polished slots in said mounting block.

8. A biaxial shear force gauge, as ser forth in claim 7, wherein:
   a. said test specimen of said preselected ablative material is bonded to said low inertial mounting block member;
   b. and, said housing guard member of said same preselected ablative material is bonded to said water-cooled container/housing.

9. A biaxial shear force gauge, as set forth in claim 8, wherein said bonding of said test specimen and of said housing guard member that are made of said same preselected ablative material is made with a room temperature vulcanizing bonding material.

10. A biaxial shear force gauge, as set forth in claim 9, wherein said gauge further includes a shock-mounting means, with this means connected to said water-cooled container/housing and simultaneously also connected to a fixed structure in said high temperature flow.

* * * * *